US010336670B2

(12) United States Patent
Haritonov et al.

(10) Patent No.: US 10,336,670 B2
(45) Date of Patent: *Jul. 2, 2019

(54) METHOD FOR PRODUCING HIGH-OCTANE COMPONENTS FROM OLEFINS FROM CATALYTIC CRACKING

(71) Applicant: AKTSIONERNOE OBSCHESTVO "GAZPROMNEFT—MOSKOVSKY NPZ" (AO "GAZPROMNEFT-MNPZ"), Moscow (RU)

(72) Inventors: Aleksandr Sergeevich Haritonov, Novosibirsk (RU); Konstantin Aleksandrovich Dubkov, Novosibirsk (RU); Mihail Vladimirovich Parfenov, Novosibirsk (RU); Aleskandr Stepanovich Noskov, Novosibirsk (RU); Valery Aleksandrovich Golovachev, St. Petersburg (RU); Andrei Vladimirovich Kleimenov, St. Petersburg (RU); Dmitry Olegovich Kondrashev, St. Petersburg (RU); Valentina Dmitrievna Miroshkina, Nizhegorodskoi obl. (RU); Dmitrii Petrovich Ivanov, Novosibirsk (RU); Sergey Vladimirovich Semikolenov, Novosibirsk (RU); Valery Sergeevich Chernyavsky, Novosibirsk (RU); Larisa Vladimirovna Piryutko, Novosibirsk (RU); Kristina Andreevna Rusetskaya, Moscow (RU); Sergey Evgenyevich Kuznetsov, Moscow (RU)

(73) Assignee: Aktsionernoe Obschestvo "Gazpromneft—Moskovsky NPZ" (AO Gazpromneft-MNPZ), Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 16/061,080

(22) PCT Filed: Nov. 29, 2016

(86) PCT No.: PCT/RU2016/000829
§ 371 (c)(1),
(2) Date: Jun. 11, 2018

(87) PCT Pub. No.: WO2017/099632
PCT Pub. Date: Jun. 15, 2017

(65) Prior Publication Data
US 2018/0370883 A1    Dec. 27, 2018

(30) Foreign Application Priority Data

Dec. 9, 2015 (RU) .................. 2015152593

(51) Int. Cl.
*C07C 45/28* (2006.01)
*C07C 1/22* (2006.01)
(Continued)

(52) U.S. Cl.
CPC ............... *C07C 27/16* (2013.01); *C07C 1/22* (2013.01); *C07C 29/136* (2013.01);
(Continued)

(58) Field of Classification Search
CPC ......... C07C 45/28; C07C 45/45; C07C 45/73; C07C 27/16; C07C 1/22; C01L 1/16; C01L 10/10
See application file for complete search history.

(56) References Cited

U.S. PATENT DOCUMENTS

| 3,932,518 A | 1/1976 | Arpe |
| 4,329,516 A | 5/1982 | Al-Muddarris |

(Continued)

FOREIGN PATENT DOCUMENTS

| CA | 2 530 219 A1 | 2/2005 |
| DE | 1 224 294 B | 9/1966 |

(Continued)

OTHER PUBLICATIONS

V. E. Taraban'ko et al.: Novel high-octane components of plant-based gasolines: Journal of Siberian Federal University: Chemistry, 2014: vol. 1: No. 7: pp. 31-35.
(Continued)

*Primary Examiner* — Sikarl A Witherspoon
(74) *Attorney, Agent, or Firm* — Ladas & Parry LLP

(57) ABSTRACT

The invention relates to the field of petrochemistry, and specifically to a method for synthesizing high-octane oxygen containing components of motor fuel. The objects of the invention consist in variants of a method for synthesizing high-octane oxygen-containing components of motor fuel from olefin-containing gas mixtures via oxidative non-catalytic conversions using nitrous oxide, and the subsequent condensation and hydrogenation of the produced oxygenates using heterogeneous catalysts. The high-octane components according to the proposed method consist in a mixture of carbonyl compounds (ketones, aldehydes, hydroxy ketones, hydroxy aldehydes) $C_2$-$C_9$ and/or branched hydrocarbons $C_5$-$C_9$ and/or alcohols in different ratios. Depending on the production method variant, the octane number of a mixture of the proposed high-octane components consists in a value between 100 and 130 RON. The technical result consists in broadening the resource base for the production of high-octane gasolines and of a variety of environmentally-friendly high-octane additives.

32 Claims, 1 Drawing Sheet

(51) Int. Cl.

| | | |
|---|---|---|
| *C07C 27/16* | (2006.01) | |
| *C07C 29/136* | (2006.01) | |
| *C07C 45/73* | (2006.01) | |
| *C10L 1/185* | (2006.01) | |
| *C10L 1/16* | (2006.01) | |
| *C10L 1/182* | (2006.01) | |
| *C10L 10/10* | (2006.01) | |
| *C07C 29/141* | (2006.01) | |
| *C07C 29/145* | (2006.01) | |
| *C07C 45/45* | (2006.01) | |
| *B01J 21/04* | (2006.01) | |
| *B01J 21/06* | (2006.01) | |
| *B01J 21/08* | (2006.01) | |
| *B01J 23/42* | (2006.01) | |
| *B01J 23/44* | (2006.01) | |
| *B01J 23/52* | (2006.01) | |
| *B01J 23/72* | (2006.01) | |
| *B01J 23/75* | (2006.01) | |
| *B01J 23/755* | (2006.01) | |
| *B01J 29/035* | (2006.01) | |
| *B01J 29/06* | (2006.01) | |

(52) U.S. Cl.
CPC .......... *C07C 29/141* (2013.01); *C07C 29/145* (2013.01); *C07C 45/28* (2013.01); *C07C 45/45* (2013.01); *C07C 45/73* (2013.01); *C10L 1/16* (2013.01); *C10L 1/1616* (2013.01); *C10L 1/182* (2013.01); *C10L 1/185* (2013.01); *C10L 1/1857* (2013.01); *C10L 10/10* (2013.01); *B01J 21/04* (2013.01); *B01J 21/063* (2013.01); *B01J 21/08* (2013.01); *B01J 23/42* (2013.01); *B01J 23/44* (2013.01); *B01J 23/52* (2013.01); *B01J 23/72* (2013.01); *B01J 23/75* (2013.01); *B01J 23/755* (2013.01); *B01J 29/035* (2013.01); *B01J 29/06* (2013.01)

(56) References Cited

U.S. PATENT DOCUMENTS

| | | | |
|---|---|---|---|
| 4,465,870 | A | 8/1984 | Herskovits |
| 4,504,688 | A | 3/1985 | Herwig et al. |
| 4,618,725 | A | 10/1986 | Lenz |
| 6,448,457 | B1 | 9/2002 | Hesse et al. |
| 2004/0082821 | A1 | 4/2004 | Koch et al. |
| 2006/0199970 | A1 | 9/2006 | Miller et al. |
| 2008/0064883 | A1 | 3/2008 | Schlitter et al. |
| 2008/0103333 | A1 | 5/2008 | Nubel et al. |
| 2009/0014354 | A1 | 1/2009 | Knuuttila et al. |

FOREIGN PATENT DOCUMENTS

| | | |
|---|---|---|
| EP | 2 298 851 A1 | 3/2011 |
| GB | 649 680 A | 1/1951 |
| JP | 0063010738 A | 1/1988 |
| RU | 1 325 840 C | 7/1995 |
| RU | 2 050 190 CI | 12/1995 |
| RU | 2 050 195 C1 | 12/1995 |
| RU | 2 050 197 CI | 12/1995 |
| RU | 2 050 198 C1 | 12/1995 |
| RU | 2 052 446 C1 | 1/1996 |
| RU | 2 091 442 C1 | 9/1997 |
| RU | 2 227 133 | 4/2004 |
| RU | 2270155 C1 | 2/2006 |
| RU | 2 227 133 C2 | 10/2011 |
| RU | 2 183 210 C2 | 6/2012 |
| SU | 1444333 A1 | 12/1988 |
| WO | 03078370 A1 | 9/2003 |
| WO | 2005012459 A1 | 2/2005 |
| WO | 2006/053735 | 5/2006 |

OTHER PUBLICATIONS

B.A. Bolotov, et al.: Vapor-phase condensation of methanol and acetone to copper-titanium catalysts, Journal of Applied Chemistry, 1971: vol. 44: No. 10: pp. 2280-2283.
W. F. Maier, et al.: Heterogeneous Deoxygenation of Ketones: Tetrahedron Letters: vol. 22: No. 42: pp. 4227-4230: 1981.
H. Noller, el al.: Activity and Selectivity of Ni—Cu/$Al_2O_2$ Catalysts for Hydrogenation of Crotonaldehyde and Mechanism of Hydrogenation: Journal of Catalysis 85: pp. 25-30: 1984.
R. Durand, et al.: Heterogeneous Hydrodeoxygenation of Ketones and Alcohols on Sulfided NiO—$MoO_3$/$\gamma$-$Al_2O_3$ Catalyst: Journal of Catalysis: vol. 90: Issue 1: Nov. 1984: pp. 147-149.
Mshari A. Alotaibi, et al.: Hydrogenation of methyl isobutyl ketone over bifunctional Pt-zeolite catalyst: Journal of Catalysis: vol. 293: (2012): pp. 141-144.
K. Alharbi, et al.: Hydrogenation of ketones over bifunctional Pt-heteropoly acidcatalyst in the gas phase: Applied Catalysis A: Gen., 2015, vol. 504, p. 417.
DE 1 224 294 B _Espacenet English Abstract, Sep. 8, 1966.
RU 1325 840 C _English Abstract, Jul. 25, 1995.
RU 2 050 190 C1 _English Abstract, Dec. 20, 1995.
RU 2 050 195 C1 _English Abstract, Dec. 20, 1995.
RU 2 050 197 C1 _English Abstract, Dec. 20, 1995.
RU 2 050 198 C1 _English Abstract, Dec. 20, 1995.
RU 2 052 446 C1 _English Abstract, Jan. 20, 1996.
RU 2 091 442 C1 _English Abstract, Sep. 27, 1997.
RU 2 183 210 C2 _English Abstract, Jun. 10, 2002.
RU2227133_Espacenet_English_Abstract, Apr. 20, 2004.
International Search Report (ISR) and Written Opinion (WO) dated May 25, 2017 for International Application No. PCT/RU2016/000829.
RU2004119128A_Espacenet_English_Abstract_Translation, Jun. 24, 2004.
JPS6310738A_Espacenet_English_Abstract_Translation, Jan. 18, 1988.
E.V. Starokon, et al., "Liquid Phase Oxidation of Alkenes With Nitrous Oxide to Carbonyl Compound", Advanced Synthesis & Catalysis, Wiley-VCH Verlag GMBH, DE, vol. 346, No. 2-3, Jan. 1, 2004, pp. 268-274, XP002321384.
Search Report issued in corresponding application European Application No. 16873448.1, dated Dec. 3, 2018.

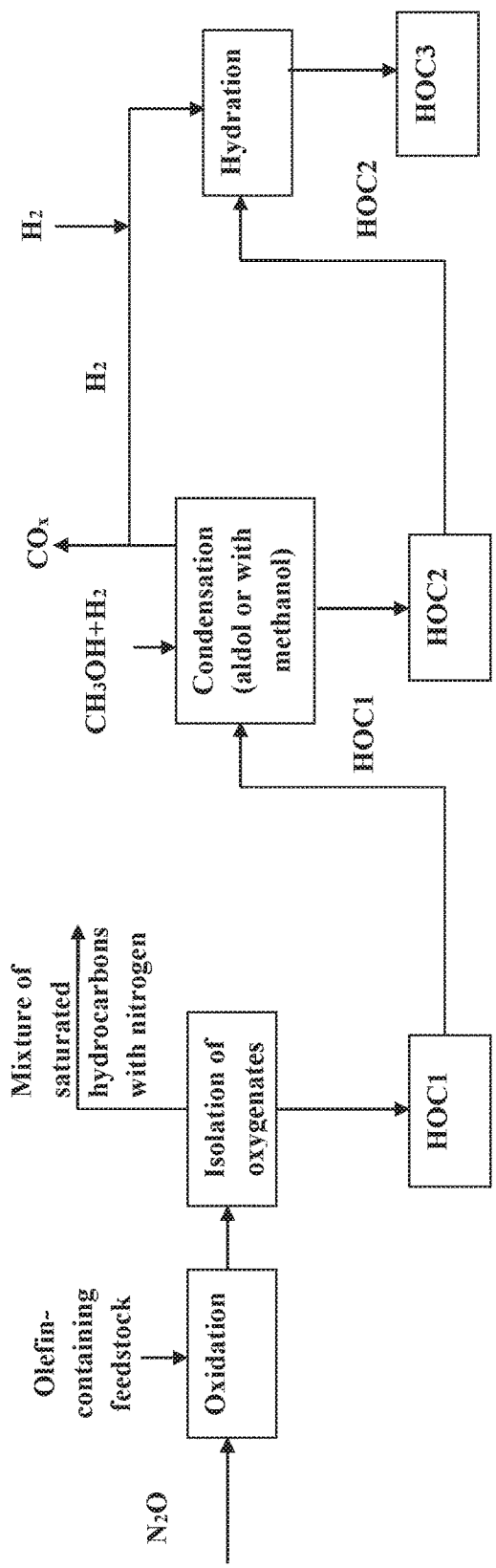

METHOD FOR PRODUCING HIGH-OCTANE COMPONENTS FROM OLEFINS FROM CATALYTIC CRACKING

RELATED APPLICATION

This application is a national phase entry under 35 USC 371 of International Patent Application No.: PCT/RU2016/000829 filed on 29 Nov. 2016, which claims priority from Russian Application No. 2015152593 filed on 9 Dec. 2015, the entire contents of which are incorporated herein by reference.

The invention relates to the field of petroleum refining and petrochemistry, and specifically to a method for synthesizing high-octane oxygen-containing components of motor fuel. The goal of the invention consists in a broadening of the resource base for the production of high-octane gasolines and a variety of high-octane additives. To achieve the goal, three embodiments of a method for producing a high-octane oxygen-containing component of motor fuel (hereinafter— the HOC) are proposed, the HOC being a mixture of $C_3$-$C_8$ carbonyl compounds (ketones, aldehydes, hydroxy ketones, hydroxy aldehydes) and/or $C_6$-$C_8$ branched hydrocarbons and/or alcohols in different ratios. The distinctive feature of the invention is that olefin-containing gaseous products obtained during the catalytic cracking of vacuum gas-oil, for example, industrial butane-butylene or propane-propylene cracking fractions, are used as a feedstock for the production of an oxygen-containing HOC of the above composition. The second feature of the proposed method for producing a HOC is use of oxidative conversions of these olefin-containing products using nitrous oxide ($N_2O$).

Use of oxygenates in commercial gasolines is a known and generally used technique of enhancing antiknock properties and improving ecological indices of a fuel. The motor gasolines standards set an obligatory content of oxygenates in the gasolines on a level of up to 2.7 wt % in terms of oxygen. Currently, alkyl tert-butyl ethers produced by reacting isobutene with a corresponding alcohol (methanol for MTBE (methyl tert-butyl ether), ethanol for ETBE (ethyl tert-butyl ether), etc.) in a liquid phase over a suitable catalyst at a pressure of 15 to 40 atm and at 60 to 100° C. have become the most commonly used high-octane additives in liquid fuel (gasoline) (see DE 1224294B, U.S. Pat. Nos. 4,329,516, 4,465,870, 4,504,688, RU 2091442, SU 1444333A1, RU 1325840C). Alkyl-tert-butyl ethers have a high blending octane number of 110 to 135 RON (research octane number). Nevertheless, a considerable disadvantage, for example, of MTBE is its good water solubility and low boiling temperature (a high pressure of saturated vapors), and its production growth is limited by an isobutylene deficit. A desirable boiling temperature of oxygenates is no less than 70 to 90° C. For example, MTAE (methyl tert-amyl ether), 120 RON, meets these requirements. Alcohol-containing ($C_1$-$C_5$ alcohols mixed with esters) additives comprising a tertiary carbon atom and capable of increasing a fuel octane number are also known. The limited resource base of aliphatic alcohols, their high hygroscopicity and their high production costs make it impossible to use such additives widely. The production of MTBE and other oxygen-containing additives in Russia is approximately 1 million tons per year while about 3 million tons per year are potentially needed. Lately, the range of available oxygen-containing high-octane additives have expanded. This is partly caused by the prohibition on using methyl tert-butyl ether in the US and the limits imposed on its use in the Western Europe countries. Bioethanol and plant-based fuel components become increasingly important as fuel (EP 2298851 A1, US 20060199970 A1, CA 2530219 A1). Carbonyl compounds have also been proposed as novel high-octane components of gasolines (V. E. Taraban'ko et al., Novel high-octane components of plant-based gasolines. JOURNAL OF SIBERIAN FEDERAL UNIVERSITY. CHEMISTRY, 2014, vol. 1, no. 7, pp. 31-35). Methyl-substituted carbonyl compounds with a branched structure are characterized by high antiknock properties. Most of carbonyl compounds with a number of carbon atoms of 3 to 9 have an octane number higher than 100 RON. As in the case of tertiary aliphatic alcohols, their use as HOCs is limited by their high cost.

The present invention provides a novel method for producing high-octane oxygenate additives based on carbonyl compounds and/or mixtures thereof with alcohols and/or branched hydrocarbons in three alternative embodiments.

A method for producing a high-octane component of motor fuels from olefin-containing gas mixtures is claimed, wherein the olefin-containing mixture is subjected to oxidation using nitrous oxide followed by an isolation of a product mixture as a high-octane component, where product gases of catalytic cracking are used as the olefin-containing mixture, said method being carried out at a temperature of 300 to 550° C. with a pressure being maintained at a level of 1 to 100 atm, and a volume ratio of the olefin-containing mixture to the nitrous oxide being maintained at a level of 2 to 10.

EMBODIMENT 1

A method for producing a high-octane component of motor fuels from olefin-containing gas mixtures is claimed, wherein the olefin-containing gas mixture is subjected to oxidation with nitrous oxide in a gas phase at the first stage, and then, at the second stage, a condensation of the products obtained at the first stage is carried out followed by an isolation of a product mixture as a high-octane component. The second stage is carried out at a temperature of 30 to 400° C. and a pressure of 1 to 10 atm. The products of the olefin fraction oxidation, before being used as a feedstock at the second stage, are subjected to separation into aldehyde and ketone fractions. The ketone and aldehyde fractions are subjected to the condensation process separately. The ketone fraction is directly used as a high-octane component, and the aldehyde fraction is subjected to the condensation process. The products of the olefin fraction oxidation, before being used as a feedstock at the second stage, are subjected to separation into individual components with their subsequent use as a target product and/or use as a feedstock for the condensation process. The second stage is carried out in a liquid phase via an aldol or aldol-crotonic condensation in the presence of any known catalyst. The second stage is carried out via a condensation with methanol in a gas phase in the presence of a copper-containing catalyst at a volume ratio of the product mixture obtained at the first stage to methanol of from 1 to 10. At the second stage, the condensation of the products obtained at the first stage with methanol is carried out in the presence of at least 0.1 vol. % of hydrogen. At the second stage, the condensation of the products obtained at the first stage with methanol is carried out in the presence of a catalyst containing 5 to 40 wt % copper on a support. $Al_2O_3$ and/or $SiO_2$, and/or $TiO_2$, and/or aluminosilicate, and/or silicate, or aluminosilicate glass fibers are used as a support for the catalysts at the second stage.

EMBODIMENT 2

A method for producing a high-octane component of motor fuels from olefin-containing gas mixtures is claimed, wherein the olefin-containing mixture is subjected to oxidation with nitrous oxide in a gas phase at the first stage; condensation of the products obtained at the first stage is carried out at the second stage; and, at the third stage, a reaction of the mixture of condensed oxygenates obtained at the second stage or the mixture of carbonyl compounds obtained at the first stage with hydrogen is carried out in the presence of a hydrogenation catalyst, followed by an isolation of a mixture of hydrogenated products as a high-octane component. The third stage is carried out at a temperature of 100 to 400° C. and a pressure of 1 to 100 atm. At the third stage, the volume ratio of the mixture of condensed products obtained at the second stage to the hydrogen of from 1 to 10 is maintained. The third stage is carried out in the presence of a supported hydrogenation catalyst comprising: 5 to 40 wt % nickel and/or 5 to 40 wt % copper and/or 5 to 40 wt % cobalt and/or 0.3 to 2 wt % palladium and/or 0.3 to 2 wt % platinum and/or 0.3 to 2 wt % gold. $Al_2O_3$ and/or $SiO_2$, and/or $TiO_2$, and/or aluminosilicate, and/or silicate, or aluminosilicate glass fibers are used as a support for the catalysts. The third stage is carried out in the presence of a mechanical mixture of a hydrogenation catalyst and an acid catalyst, with an H-form zeolite being used as the latter, the zeolite being selected from a group of zeolites including FAU, FER, MFI, MEL, BEA, MTT, and TON structures.

EMBODIMENT 3

The resource base for the production of a HOC according to the novel method is gaseous olefin-containing mixtures formed during the catalytic cracking of a vacuum gas oil. The embodiments of the method include one or two or three successive stages of refining the olefin-containing feedstock: oxidation with nitrous oxide, condensation and hydrogenation. Mixtures of oxygenates obtained in each of the stages can be used as a high-octane liquid fuel additive.

Embodiment 1 involves isolation of a HOC right after carrying out the first stage of the general three-stage process. The essence of the first stage consists in the oxidation of gaseous olefin-containing $C_2$-$C_4$ mixtures with nitrous oxide at temperatures of 300 to 550° C. As a result, the oxygen from $N_2O$ is bonded to the olefins comprised in the mixtures with a formation of $C_2$-$C_4$ carbonyl compounds (aldehydes and ketones), and the product of the conversion of $N_2O$ is molecular nitrogen. Water is not formed during the reaction. The final mixture of carbonyl compounds can already be used as a HOC for motor fuel. Unlike other methods for synthesizing carbonyl compounds from olefins (oxo process, hydration followed by dehydrogenation of alcohols, oxidation with oxygen in liquid and gas phases), the proposed method results in selective formation of carbonyl compounds in the absence of a catalyst, with a minimum of by-products and without the formation of acids, alcohols and glycols.

A number of patents disclosing the use of nitrous oxide for the olefin conversion into carbonyl compounds are known. In patent GB 649680, the reaction of nitrous oxide with olefins is carried out in a static autoclave reactor at a temperature of 250 to 500° C. and a pressure of up to 1000 atm. A disadvantage of this method is a low selectivity to carbonyl compounds, harsh process conditions, including feeding liquid nitrous oxide to the reactor. RU 2227133 discloses a method for producing a mixture of carbonyl compounds (acetone, propionic aldehyde and acetaldehyde in a molar ratio of 1:0.4:0.15) by liquid-phase oxidation of propylene with nitrous oxide in a mesitylene solution in the presence of an inert diluent gas at a temperature of up to 350° C. and a $N_2O$ pressure of up to 100 atm. The disclosed methods for producing carbonyl compounds by liquid-phase oxidation of olefins using nitrous oxide have a number of general disadvantages: the oxidation process is carried out under very harsh conditions, the process is slow even at high temperatures and pressures, batch operation mode, the necessity of using a solvent, and only individual olefins are suitable for oxidation.

The present patent discloses a method for producing a mixture of carbonyl compounds ($C_2$-$C_4$ aldehydes and ketones) starting from an olefin-containing feedstock, said method being devoid of the disadvantages mentioned above. At the same time, the reaction product can be used as a HOC of a gasoline. This method is carried out by gas-phase oxidation of $C_2$-$C_4$ alkane-olefin mixtures, for example, hydrocarbon gases from the thermal and/or catalytic cracking process, using nitrous oxide ($N_2O$) at 300 to 550° C. in a flow mode, without their preliminary separation into separate components. In particular, products of fractionating the reaction mixture of thermal and/or catalytic cracking process, for example, a propane-propylene fraction and/or a butane-butylene fraction, are used as a feedstock. The butane-butylene fraction can be used as a feedstock as well, after recovering the methanol and/or ethanol isobutene etherification product therefrom for the synthesis of MTBE and ETBE (in this case, the olefin-containing mixture for oxidation with nitrous oxide can also be used without the recovery of methanol and/or ethanol). Using a butane-butylene mixture, instead of individual butenes, as a feedstock for the synthesis of a HOC allows for a substantial reduction of the material costs, as the very energy-consuming process of isolating individual components is eliminated.

Nitrous oxide can be used both in pure form and with impurities, the presence of which is due to the method of its preparation. The olefin content in the $C_2$-$C_4$ alkane-olefin mixture may vary within a wide range. The lower limit for the olefin content in the mixture is determined only by economic expediency and by the necessity to meet explosion-safe process conditions.

Carrying out the process in a gas phase in the flow mode allows an easy control of the reaction rate by adjusting the temperature and pressure that, unlike the liquid-phase static processes in autoclaves, are not limited by the phase equilibrium conditions and can vary independently. There is no tar in the oxidized product in the case of synthesizing a HOC from gaseous $C_2$-$C_4$ olefin-containing mixtures.

When oxidizing mixtures comprising terminal olefins (ethylene, propylene, 1-butene, isobutene), cyclopropane derivatives are additional valuable products of the $C_2$-$C_4$ olefins conversion. For example, when propane-propylene mixtures are oxidized, methylcyclopropane ($C_4$ hydrocarbon) is formed, and dimethylcyclopropanes and ethylcyclopropane ($C_5$ hydrocarbons) are formed when butane-butene mixtures are oxidized. Substituted cyclopropanes have an octane number (RON) at a level of 103 to 104 units and are valuable compounds that can also be used for compounding motor gasolines.

According to the claimed method, the starting alkane-olefin mixture of $C_2$-$C_4$ hydrocarbons is mixed with nitrous oxide in a ratio that eliminates the formation of explosive mixtures. Hydrocarbon-rich mixtures with nitrous oxide are explosion-proof under normal conditions. As the concentration limits expand with increasing temperature and pressure, it is recommended to oxidize the butane-butene mixture at a concentration of nitrous oxide in the mixture with $C_2$-$C_4$ hydrocarbons no more than 30 vol. %.

Thus, according to the present invention, in order to produce a HOC according to embodiment 1, a gas-phase oxidation of mixtures of $C_2$-$C_4$ olefins and alkanes to aldehydes and ketones using nitrous oxide is carried out without a catalyst in the flow-type reactor at temperatures of 300 to 550° C., a pressure of 1 to 100 atm and a contact time (residence time of the reaction mixture in the reactor) of 0.01 to 60 minutes (based on normal conditions). It is more preferable to carry out the process at temperatures of 350 to 450° C., a pressure of 10 to 50 atm, and a contact time of 0.2 to 20 minutes (under normal conditions). The process can be carried out in an isothermal or adiabatic mode.

Since nitrous oxide reacts only with olefins and does not react with alkanes and the reaction products (aldehydes, ketones, cyclopropane derivatives) under the conditions used, the oxidation can be carried out to achieve high values of olefin conversion, with no significant reduction of selectivity to carbonyl compounds and substituted cyclopropanes.

The reaction mixture leaving the reactor is cooled. Nitrogen gas is blown off, and the condensed products, which are predominantly a mixture of $C_2$-$C_4$ carbonyl compounds, are used as a HOC. The composition of the HOC is determined by the composition of the starting olefin-containing mixture and the degree of olefin conversion during the oxidation with nitrous oxide. Olefin-containing $C_2$-$C_4$ gases result in a mixture of aldehydes and ketones of the following composition: acetaldehyde, propanal, butanal, acetone and methyl ethyl ketone. It is possible to isolate separate carbonyl compounds or to enrich the mixture with high-boiling components by any of the known methods: rectification, extractive distillation, recrystallization, etc. The advantage of the proposed method for oxidizing olefins with nitrous oxide is the absence of water in the reaction products. This fact facilitates isolation of individual carbonyl compounds by rectification, since water forms azeotropic mixtures with most such compounds. The hydrocarbon mixture with the unreacted olefin residue and conversion by-products can be used as a component of liquefied gas fuels.

Embodiment 2 of the claimed method for producing a HOC includes two stages. The first stage is analogous to the oxidation stage of the $C_2$-$C_4$ olefin-containing gas mixture with nitrous oxide according to embodiment 1. It is carried out under the same conditions and leads to the formation of a mixture of $C_2$-$C_4$ carbonyl compounds. At the second stage, condensation of the mixture of $C_2$-$C_4$ carbonyl compounds obtained at the first stage is carried out to 1) increase the molecular weight of the carbonyl compounds, i.e. the number of carbon atoms in the molecule, and, as a consequence, increase the boiling temperature of the substances, and 2) increase branching of the carbon chains present in the mixture of carbonyl compounds. At the same time, the problem of increasing stability of a HOC is simultaneously solved by substituting the hydrogen atom active with respect to the condensation reactions at the α-carbon atom in the carbonyl compound. This substitution greatly slows the processes of further condensation of carbonyl compounds and formation of tar. Stability of the HOC also increases as a result of complete removal of the lowest-boiling product, which is acetaldehyde (boiling temperature is 20.8° C.), from the HOC, said product, in view of its high reactivity, being condensed first with a formation of a crotonaldehyde and a paraldehyde with 120 RON.

There are two possible methods of carrying out the second stage, i.e. the condensation process according to embodiment 2 of the method for producing a HOC. The first method (method 2-1) involves carrying out aldol or aldol-crotonic condensation in a liquid phase in the presence of any known alkaline catalyst (alkalis, alkali or alkali-earth metal salts, alkali-earth oxides, hydrotalcites, amines, etc.) or an acid catalyst (inorganic acids, zeolites, ion exchange resins). In this case, the condensation is carried out in a reactor with a reflux condenser and a reflux column or in a Soxhlet-type extractor with accumulation of higher-boiling reaction products in the main reactor.

A temperature in the reactor is 5 to 100° C., depending on the composition of the starting mixture of carbonyl compounds passed to the condensation. Thus, in $C_2$-$C_4$ aldehydes are predominately being present in the mixture, the temperature in the condensation reactor should not exceed 40 to 50° C. And vice versa, in case of ketone condensation, it is expedient to raise the temperature in the reactor to 70 to 80° C. As a result, a mixture of oxygenates is formed, mainly consisting of branched unsaturated $C_3$-$C_8$ aldehydes and ketones, hydroxyaldehydes and hydroxyketones, a paraldehyde and derivatives thereof.

It is known that aldehydes are easier to undergo condensation reactions than ketones. This difference results in a predominant conversion of light aldehydes to higher-boiling aldehydes and paraldehyde, as compared with ketones. Therefore, as a result of the condensation, the content of aldehyde groups (both absolute and relative) in the mixture decreases as compared with ketone groups. This decrease promotes a chemical stability of the produced HOC. As the hydrocarbon chain of the carbonyl compounds grows, water solubility of the respective compounds decreases, which fact is advantageous for their use as a HOC components. Low water solubility is a favorable property for using a substance as a high-octane fuel additive.

The second method for carrying out the condensation stage according to embodiment 2 of the method for producing a HOC (method 2-2) according to the invention involves carrying out a process of condensation of the mixture of carbonyl compounds obtained at the first stage with methanol. Such condensation reactions are based on α-methylation reaction of the carbonyl compounds with methanol. The goal of this stage is 1) to increase the molecular weight of the carbonyl compounds, 2) to increase the boiling temperature, 3) to increase the branching degree of the carbon chain of the carbonyl compound, and 4) to deactivate the hydrogen atom at the α-atom of the carbonyl compound so as to increase the chemical stability of the HOC. The method for synthesizing higher ketones from lower ketones based on the alpha-methylation reaction of the ketones with methanol is known, although it has not been implemented in industry (B. A. Bolotov, V. L. Klyuev. Vapor-phase condensation of methanol and acetone to copper-titanium catalysts, JOURNAL OF APPLIED CHEMISTRY, 1971, vol. 44, no. 10, pp. 2280-2283; U.S. Pat. No. 3,932,518, C07C37/20, 1976; U.S. Pat. No. 4,618,725, B01J23/00, 1986). The chemical essence of this method consists in dehydrocondensation of a ketone and methanol, i.e. in alkylation (methylation) of ketones at the α-position in respect of the carbonyl group. Such process was carried out in a vapor-gas phase under relatively mild conditions (atmospheric pressure, temperatures up to 300° C.) in the presence of $CuO/TiO_2$ catalyst comprising 15 to 80 wt % of copper oxide on titanium oxide. According to this method, branched ketone impurities (methyl isopropyl ketone, ethyl isopropyl ketone, and diisopropyl ketone) were formed along with methyl ethyl ketone (the primary and main product of the acetone condensation). To achieve an acceptable acetone conversion, the process was carried out with a long contact time of up to 23 s. The total yield of ketones did not exceed 50% on the CuO/TiO$_2$ catalyst, and the methylation proceeded predominantly at a single methyl group of acetone with a predominant formation of methyl ethyl ketone and methyl isopropyl ketone. This work has not got any further development, may be due to the low activity of the catalyst.

In the patent to Hoechst Aktiengesellschaft (U.S. Pat. No. 3,932,518, C07C 45/00, Jan. 13, 1976), principal possibility of cyclohexanone methylation in a gas phase at 250 to 500° C. in the presence of copper- and/or silver-containing catalysts is claimed. BASF AG company (Germany) published a patent (U.S. Pat. No. 4,618,725, C07C 45/71, Oct. 21, 1986), where synthesis of alpha-methyl-substituted ketones was carried out at relatively high temperatures of 350 to 500° C., with pressures of 1 to 20 atmospheres and contact times of 6 to 20 s with water vapor additives. Massive metal oxides (Ce, Cr, Fe, Mg, Mn) without a support were used as catalysts. In all the above patents, the reaction of ketones with methanol is carried out on oxide heterogeneous catalysts, at temperatures of 250 to 500° C. As a result of the reaction, a mixture of linear and branched aliphatic or unsaturated or cyclic or aromatic ketones is produced. The produced higher ketones can be separated from low-boiling products that are returned to the reaction. The main disadvantage of the known method is the necessity of carrying out the process with long contact times and in the presence of an oxygen-containing gas.

None of the patents provides data on the duration of the experiments, and there is no information on the deactivation of the catalysts. This makes it impossible to assess the operation stability of the catalysts, i.e. the time of their run between regenerations, and the potential of this reaction for use in practice. In addition, the patents do not take into account the possibility of methylation of aldehydes or mixtures of ketones with aldehydes. In view of the high activity of aldehydes in self-condensation reactions, it was impossible to predict efficiency and depth of methylation in mixtures of aldehydes and ketones in advance. Thus, it was impossible to foresee the reaction direction during the condensation of mixtures of various carbonyl compounds with methanol in order to produce a HOC.

According to the invention, the condensation of ketones with methanol for extending their carbon chain according to method 2-2 of producing a HOC is carried out in the presence of hydrogen, which results in a greater process efficiency, as compared with the methods described above. To this end, the starting mixture of carbonyl compounds obtained at the first stage of oxidation of olefin-containing mixtures with nitrous oxide is mixed with methanol in a ratio of 1:1 to 1:10, hydrogen and a diluent gas, and then it is passed through a layer of copper-containing heterogeneous catalyst at 150 to 400° C. Either of the gases listed below or a mixture thereof is used as the diluent gas: nitrogen and/or any inert gas and/or carbon dioxide. Up to 5 vol. % of hydrogen can be added in the diluent gas.

The optimal temperature in the reactor must ensure that the process proceeds in the gas phase. It depends on the composition of the starting mixture of carbonyl compounds and the boiling temperatures of the starting compounds and the reaction products. When such approach is used to synthesize individual carbonyl compounds with an extended carbon chain, it is necessary to carefully control the hydrogen content in the mixture so as to avoid a hydrogenation of the carbonyl compounds to alcohols and hydrocarbons. When a HOC is produced, such a limitation is eliminated, as the presence of alcohols and hydrocarbons having a branched structure in the reaction products can result in an increase of the octane number and the chemical stability of the produced HOC.

Furthermore, an important advantage of the claimed method is that even a small hydrogen content in the starting reaction mixture at the level of 0.1 vol. % reduces the catalyst deactivation rate significantly and increases its run between regenerations several-fold. The catalyst stability can also be significantly increased by increasing the pressure in the reaction mixture to 20 atm.

It is also important to select the contact time of the reaction mixture with the catalyst. This parameter varies from 0.1 to 20 s, preferably from 1 to 5 s. If it is necessary to obtain products with a high branching, the contact time increases to 6 to 20 seconds. Thus, in order to produce a HOC, the reaction can be carried out with different degrees of the starting carbonyl compounds methylation, which is achieved by varying temperature, contact time, and an amount ratio of the carbonyl compounds and methanol. A higher methylation degree can also be achieved by recycling low-boiling low-branched carbonyl compounds to the reactor for their remethylation.

The claimed method allows using any of the known catalysts comprising copper or a copper oxide, both massive and supported. Such catalysts can be prepared using any inorganic or organic copper salt and any of the known supports: alumina, alkali-earth metal oxides, amorphous metallosilicates, crystalline metallosilicates, silicalite, mesoporous silicates and metallosilicates, silica gel, woven glass fabrics, carbon and polymer supports. The catalysts can include promoters selected from certain alkaline and alkali-earth metals and certain transition metals in amounts of 0.1 to 5.0 wt % based on the copper amount. The copper content in the catalyst may vary from 1 to 50 wt %, preferably in a range of 5 and 30 wt % based on the catalyst weight. A large amount of copper in the catalyst, on one hand, increases its activity but, on the other hand, leads to an undesirable consumption of methanol in a steam conversion side reaction that leads to carbon oxides formation.

Thus, according to the invention, the second method for carrying out the condensation stage according to embodiment 2 of the method for producing a HOC (method 2-2) involves extending and branching the carbon chain of the carbonyl compounds via their methylation reaction with methanol, with the essential and main difference being that the reaction is carried out in the presence of hydrogen and at an elevated pressure. Adding hydrogen to the starting reaction mixture makes it possible to increase the time of the catalyst run between regenerations several-fold and, consequently, to increase the amount of the HOC produced per unit of the reactor volume. Furthermore, in addition to the carbonyl compounds in the composition of the HOC produced according to this method, new compounds with a high RON values are formed: alcohols and branched hydrocarbons. The introduction of hydrogen into the reaction mixture maintains the catalyst in the reduced state. A positive effect of the hydrogen addition is most clearly shown when the process is carried out over a catalyst with a low copper content. Therefore, an additional advantageous effect of the hydrogen addition to the reaction mixture consists in the possibility of reducing the copper content in the catalyst and reducing the catalyst charge in the reactor, and also increasing selectivity of the process in respect of the methanol conversion.

Embodiment 3 of the method for producing a HOC consists of three stages. The first stage is analogous to the stage of oxidation of the olefin-containing gas mixture with nitrous oxide according to embodiment 1, the second stage is analogous to the condensation stage according to embodiment 2 (methods 2-1 and 2-2). Both stages are carried out under the same conditions as in embodiments 1 and 2, and they result in the formation of a HOC. In this particular case, the HOC is a mixture of carbonyl compounds, oxycarbonyl compounds, a paraldehyde and derivatives thereof, provided the aldol condensation (method 2-1) is carried out at stage 2, or a mixture of carbonyl compounds, alcohols and branched hydrocarbons, when the condensation with methanol (method 2-2) is carried out. At the third stage, a hydrogenation of the HOC obtained at the second stage is carried out so as to increase its stability and to control the oxygen content therein. The HOC produced according to embodiment 3 comprises a mixture of aliphatic carbonyl compounds and/or a mixture of aliphatic alcohols and/or a mixture of saturated hydrocarbons having a branched structure. The HOC produced according to embodiment 1 from the olefin-containing gas mixture can also be fed to the hydrogenation stage.

As it has already been disclosed, most carbonyl compounds with 3 to 9 carbon atoms have an octane number higher than 100 RON. The HOC produced according to embodiment 2 is predominantly a mixture of carbonyl compounds. However, high reactivity of the carbonyl compounds, especially aldehydes, is a disadvantage that limits their usage as a HOC. In particular, a number of carbonyl compounds, aldehydes in the first place, exhibit a high activity in the aldol condensation reactions, facilitating tar formation. Therefore, conversion of the carbonyl compounds to more stable alcohols in the HOC composition facilitates an increase in the chemical stability of gasolines. In addition, according to the Technical Regulations of the Customs Union, oxygen content in a gasoline should not exceed 2.7 wt %. Therefore, hydrogenation of the methyl-substituted carbonyl compounds to corresponding branched hydrocarbons provides a solution for the problem of the HOC oxygen content reduction while maintaining its anti-knock properties. Carrying out the hydrogenation stage according to embodiment 3 allows a smooth control of the oxygen content in the HOC and, at the same time, increasing chemical stability thereof.

A number of catalysts are known that carry out the process of hydrogenation of carbonyl compounds, predominantly to alcohols. However, these catalysts have a number of serious disadvantages. Thus, $Ni/Al_2O_3$ and $Ni—Cu/Al_2O_3$ catalyst (Tetrahedron Lett., 1981, 22, 4227; Journal of Catalysis, 1984, 85, 25-30) has a reduced activity with respect to branched ketones sterically hindered for hydrogenation. Other widely used catalysts based on supported metal sulfides require harsh reaction conditions (T≥300° C., P≥100 atm) (Journal of Catalysis, 1984, 90, 147-149).

A large number of patents are aimed at synthesizing highly active catalysts based on copper chromite and copper oxide on various supports (RU 2050198, RU 2050197, RU 2050195, RU 2052446, RU 2183210, WO 2006053735 A1, US 2008103333, US 2008064883, US 2004082821, U.S. Pat. No. 6,448,457), said copper chromite and copper oxide being modified using transition and alkali-earth metals selected from a wide range of compounds. Disadvantages of such catalysts are their complex composition that makes their synthesis and use impractical from the technological point of view, and difficulties with controlling alcohol to alkane ratio, said substances being the main products of the carbonyl compounds hydrogenation. To synthesize a HOC with an optimal composition, a catalytic system is required that makes it possible to fine-tune this ratio.

To increase selectivity to the corresponding hydrocarbon, bifunctional catalysts comprising metals with a hydrogenating function and introduced into a support having a dehydrating effect are used. Examples of platinum catalysts based on modified heteropolyacids or zeolites with a MFI, BEA and Y structure are known (M. A. Alotaibi, E. F. Kozhevnikova, I. V. Kozhevnikov. Hydrogenation of methyl isobutyl ketone over bifunctional Pt-zeolite catalyst, J. Catal, 2012, vol. 293, p. 141; K. Alharbi, E. F. Kozhevnikova, I. V. Kozhevnikov. Hydrogenation of ketones over bifunctional Pt-heteropoly acid catalyst in the gas phase, Applied Catalysis A: Gen., 2015, vol. 504, p. 417). The necessity to preserve the dehydrating function of the support, particularly with regard to zeolites, requires an introduction of a very small amount of metal. It is known that only noble metals can provide a high activity of a hydrogenation catalyst with their content at a level of 0.5 to 2 wt %. Patent RU 2050190 discloses a method for synthesizing a low-percentage nickel catalyst modified with heteropolycompounds of a different composition for hydrogenation processes, including carbonyl compounds. The complexity of the heteropolycompounds synthesis and the low stability of their salts can be mentioned as disadvantages of the catalyst.

According to the invention, the third hydrogenation stage for producing a HOC according to embodiment 3 is carried out with an excess of hydrogen in a gas-phase mode at 100 to 400° C., at a pressure of 1 to 100 atm, with any of the known hydrogenation catalysts being charged to the reactor, preferably the catalyst comprising 5 to 40 wt % nickel, and/or copper, and/or cobalt, and/or from 0.3 to 2 wt % palladium, and/or platinum, and/or gold on a support. To this end, any of the known supports, preferably $Al_2O_3$ and/or $SiO_2$, and/or $TiO_2$ and/or aluminosilicate and/or silicate or aluminosilicate glass fibers, are used.

The main and essential difference of the third hydrogenation stage for producing a HOC according to embodiment 3 of the claimed invention from the traditional hydrogenation processes of carbonyl compounds is that, in addition to the hydrogenation catalyst, a dehydration catalyst is charged to the reactor. The use of a mechanical mixture of the hydrogenation catalyst of the carbonyl compound and the dehydration catalyst of the obtained alcohol allows increasing the chemical stability of the HOC obtained at the second stage and to control the oxygen content therein. In addition, the use of the mechanical catalyst mixture allows separating hydrogenating and dehydrating catalyst functions and using relatively cheap oxide hydrogenation catalysts based on copper and nickel with a high content of the active metal of 10 to 50 wt %. When trying to combine these two functions in a single catalyst (fixing the corresponding catalytically active metals on a single support), it can be expected that a high concentration of the hydrogenating active component will inevitably have an adverse effect on the dehydrating catalyst function as a result of blocking or neutralizing the acid sites and vice versa.

According to the proposed method, a whole range of known support oxides can be used as a support for the hydrogenation catalyst. Any heterogeneous catalyst of acidic nature, preferably zeolites, can be used as a dehydrating component of the mixed catalyst. The best result is achieved when using an H-form zeolite of any structure selected from MFI, Y, BEA, FER, MTT, and TON. The use of zeolites not modified with a hydrogenating metal allows an easy control of the alcohol to hydrocarbon ratio in the HOC. To this end, the zeolite content in the composite or its acidity are varied by using zeolites of different chemical compositions and structures.

The application US 2009014354A1 can be considered as the closest prior art for the claimed invention, said application disclosing a process of producing a base oil from a non-oil feedstock. One of the stages of this process is a hydrodefunctionalization reaction with a simultaneous isomerization of an oxygen-containing feedstock so as to obtain branched hydrocarbons. The reaction is carried out in the presence of bifunctional catalysts based on a molecular sieve selected from zeolites or silicoaluminophosphates with an introduced metal having a hydrogenating function, said metal being selected from metals of groups 8 to 10 of the Periodic system. The authors specifically note that, along with the hydrogenation of the carbonyl compounds, this catalyst carries out the isomerization and cracking processes of the produced hydrocarbons with a formation of up to 30 wt % light $C_1$-$C_4$ hydrocarbons.

The main difference of the approach proposed in the invention consists in the possibility of minimizing the isomerization and cracking of methyl-substituted branched alkanes processes simply by varying the charge ratio of the hydrogenation catalyst with the known hydrogenating activity (properties) and an unmodified H-form zeolite with the known dehydrating activity (properties). As a result, the activity, selectivity and operation stability of the catalysts for hydrogenation of branched ketones to the corresponding branched alkanes and/or alcohols and/or mixtures thereof are increased. An additional advantage of the claimed method according to embodiment 3 is the possibility of controlling the qualitative and quantitative composition of the final product, and specifically a HOC.

The essence of the invention is illustrated by the following examples, tables and drawing.

The FIGURE illustrates a principal scheme for producing a high-octane component, wherein:

HOC1 is a high-octane component according to embodiment 1;

HOC2 is a high-octane component according to embodiment 2;

HOC3 is a high-octane component according to embodiment 3.

EMBODIMENT 1

Example 1

Butane-butene fraction of the catalytic cracking process having the butene content of 87.4 vol. % and the butane content of 12.1% is mixed with nitrous oxide in a ratio of 9:1. The reaction mixture is passed through a stainless steel reactor having a volume of 25 cm³ at a pressure of 1 atm, with the temperature of 400° C. being maintained in the reactor. The feed rate of the mixture is 25 cm³/min (under normal conditions). The results of the experiment are given in Table 1. Here, the reaction temperature (T), nitrous oxide conversion ($X_{N2O}$), total olefin conversion ($X_R$), total ketone and aldehyde productivity (Pr), and total selectivity to carbonyl products ($S_\Sigma$), which approaches 100%, are provided. The main product of the reaction is methyl ethyl ketone (MEK), which is formed with a selectivity of 44.8%. Along with MEK, acetone (A) is formed with a selectivity of 17.5%, propanal (PA) is formed with a selectivity of 17.5%, acetaldehyde (AA) is formed with a selectivity of 11.3%, isobutanal (i-BA) is formed with a selectivity of 4.6%, and butyraldehyde (BA) is formed with a selectivity of 4.3%, dimethyl- and ethylcyclopropanes are also formed.

After the unreacted gases are separated, the final mixture of carbonyl compounds and substituted cyclopropanes is used as a high-octane additive. The octane number of the obtained mixture of 5 wt % HOC with gasoline AI-92 (92.1 RON and 83.7 MON (motor octane number)) is 93.6 RON and 85.2 MON with the oxygen content being 1.1 wt %. The content of actual tar is 1.8 mg/100 cm³. Thus, the blending octane number of the HOC produced according to this example is 122.1 RON and 113.5 MON.

Example 2

The reaction is carried out similarly to Example 1, with the difference being that the reaction temperature is set at 500° C. Table 1 (example 2) shows the results. One can see that the performance of the volume unit of the reactor increases to 1.4 g/l per hour, the total selectivity to carbonyl compounds is 93.8%. The octane number of the obtained mixture of 10 wt % HOC with gasoline AI-92 (92.1 RON and 83.7 MON) is 93.5 RON and 85.2 MON with the oxygen content being 2.2 wt %. The content of actual tar is 2.0 mg/100 cm³. Thus, the blending octane number of the HOC produced according to this example is 120.1 RON and 109.7 MON.

Example 3

The experiment is carried out in the same manner as in Example 1, with the difference being that the reaction temperature is set at 500° C. Table 1 (example 3) shows the results. One can see that the performance of the volume unit of the reactor increases to 1.4 g/l per hour, the total selectivity to carbonyl compounds is 77.1%. The octane number of the obtained mixture of 10 wt % HOC with gasoline AI-92 (92.1 RON and 83.7 MON) is 93.2 RON and 84.7 MON with the oxygen content being 2.2 wt %. The content of actual tar is 2.7 mg/100 cm³. Thus, the blending octane number of the HOC obtained in this example is 114.1 RON and 103.7 MON.

Example 4

The experiment is carried out in the same manner as in Example 1, with the difference being that the temperature in the reactor is maintained at 400° C., and the pressure of the reaction mixture is 10 atm. Table 1 (Example 4) shows the results. One can see that an increase in the reactor pressure results in an increase in the reactor performance in what concerns the carbonyl compounds. The octane number of the obtained mixture of 10 wt % HOC with gasoline AI-92 (92.1 RON and 83.7 MON) is 93.7 RON and 85.0 MON with the oxygen content being 2.2 wt %. The content of actual tar is 0.8 mg/100 cm³. Thus, the blending octane number of the HOC produced according to this example is 124.1 RON and 109.7 MON.

Example 5

The experiment is carried out in the same manner as in Example 1, with the difference being that the temperature in the reactor is maintained at 400° C., and the pressure of the reaction mixture is 70 atm. Table 1 (Example 5) shows the results. One can see that an increase in the reactor pressure results in a substantial increase in the reactor performance in what concerns the carbonyl compounds. The octane number of the obtained mixture of 10 wt % HOC with gasoline AI-92 (92.1 RON and 83.7 MON) is 93.7 RON and 85.2 MON with the oxygen content being 2.2 wt %. The content of actual tar is 0.9 mg/100 cm$^3$. Thus, the blending octane number of the HOC obtained according to this example is 124.1 RON and 113.7 MON.

Example 6

The experiment is carried out in the same manner as in Example 4, with the difference being that the butane-butene fraction of the catalytic cracking process is mixed with nitrous oxide in a ratio of 7:3. An increase from 10 mol. % to 30 mol. % in the nitrous oxide content in the reaction mixture is accompanied by a more than twofold increase in the reaction volume unit performance with an insignificant decrease in the total selectivity to carbonyl compounds (less than 2%). The octane number of the obtained mixture of 10 wt % HOC with gasoline AI-92 (92.1 RON and 83.7 MON) is 93.6 RON and 85.0 MON with the oxygen content being 2.2 wt %. The content of actual tar is 1.2 mg/100 cm$^3$. Thus, the blending octane number of the HOC obtained in this example is 122.1 RON and 109.7 MON.

Example 7

Example 7 describes the oxidation of propane-propylene fraction of the catalytic cracking process. The experimental conditions and results are given in Table 1. The main products of the oxidation are carbonyl compounds: acetone (A); acetaldehyde (AA); and propanal (PA). The total selectivity to the carbonyl compounds, depending on the reaction conditions, is 86.7% at 350° C. and 4 atm and 74.6% at productivity of 0.3 g/l·h. The octane number of 10 wt % obtained HOC with gasoline AI-92 (92.1 RON and 83.7 MON) is 94.3 RON and 85.5 MON with the oxygen content being 2.7 wt %. The content of actual tar is 0.8 mg/100 cm$^3$. Thus, the blending octane number of the produced HOC is 136.1 RON and 119.7 MON.

Example 8

The experiment is carried out in the same manner as in Example 7, with the difference being that the temperature in the reactor is maintained at 450° C., and the pressure of the reaction mixture is 7 atm. Table 1 (Example 8) shows the results. One can see that an increase in the reactor temperature and pressure results in an increase in the reactor performance in what concerns the carbonyl compounds, but is accompanied by a decrease in selectivity. The octane number of 10 wt % obtained HOC with gasoline AI-92 (92.1 RON and 83.7 MON) is 94.0 RON and 85.2 MON with the oxygen content being 2.2 wt %. The content of actual tar is 1.0 mg/100 cm$^3$. Thus, the blending octane number of the produced HOC is 130.1 RON and 113.7 MON.

EMBODIMENT 2

Example 9

70 ml/min of the mixture of carbonyl compounds obtained according to embodiment 1 (Example 2) (20 vol. %), methanol (60 vol. %) and argon (20 vol. %/) are passed through a 2.0 cm$^3$ catalyst bed at a temperature of 250° C. for 10 hours. The catalyst has a composition of 28 wt % CuO and 72 wt % SiO$_2$. The composition of the reaction mixture is determined by a direct sampling from the vapor-gas flow with a subsequent analysis of organic components in a flame ionization detector and inorganic components in two thermal conductivity detectors. The organic components of the reaction mixture are separated in a capillary column DB-1701. The obtained mixture contains ketones and aldehydes, in particular, methyl ethyl ketone, diethyl ketone, methyl isopropyl ketone, ethyl isopropyl ketone, methyl isobutyl ketone, propanal, 2-methylpropanal, 2,2-dimethylpropanal, 2-methylbutanal, and 2,2-dimethylbutanal.

Productivity (Pr) for methylated ketones and aldehydes was used as an activity characteristic:

$$Pr \text{ (g methylated ketone or aldehyde/g catalyst per hour)} = (\Sigma(N_{MK}-M_{MKi}))\cdot 60/m;$$

wherein:
 $N_{MK}$ is the total flow of the reaction mixture at the reactor outlet, mol/min;
 $M_{MKi}$ is the molecular weight of the methylated ketone or aldehyde, g/mol;
 m is the weight of the catalyst charged to the reactor, g.
Selectivity (S) of formation of the sum of methylated ketones or aldehydes from the starting carbonyl compound is calculated by the formula:

$$S \text{ (\%)} = 100 \cdot (\Sigma N_{MKi})/(N_K^0 - N_K);$$

wherein:
 $N_{MKi}$ is the flow of methylated ketones or aldehydes, mol/min;
 $N_K^0$ is the inflow of the mixture of carbonyl compounds, mol/min;
 $N_K$ is the outflow of the mixture of carbonyl compounds, mol/min.

The time required to reduce the productivity for the sum of methylated carbonyl compounds twofold is used as a parameter characterizing the catalyst operation stability. After the reaction is completed, the obtained mixture of carbonyl compounds, water and methanol is condensed, the unreacted methanol and acetone are distilled from the mixture and used as a HOC after drying. The octane number of 3.9 wt % obtained HOC with gasoline AI-92 (92.6 RON and 84.0 MON) is 93.6 RON and 84.5 MON with the oxygen content being 1.4 wt %. The content of actual tar is 3.1 mg/100 cm$^3$. Thus, the blending octane number of the produced HOC is 118.3 RON and 96.9 MON.

Example 10

The reaction is carried out in the same manner as in Example 9, with the difference being that a portion of argon is substituted with hydrogen. The starting reaction mixture, as a whole, contains 4 vol. % hydrogen. The results of testing the catalyst are shown in Table 2. One can see that, as compared with Example 9, the catalyst operation time to a twofold decrease in the activity was almost 4 times longer. The final mixture of carbonyl compounds has a similar composition, but, at the same time, the content of alcohol impurities increases. The octane number of 6.6 wt % obtained HOC with gasoline AI-92 (92.6 RON and 84.0 MON) is 93.4 RON and 84.2 MON with the oxygen content being 1.6 wt %. The content of actual tar is 1.2 mg/100 cm$^3$. Thus, the blending octane number of the produced HOC is 104.7 RON and 87.0 MON.

Example 11

100 ml of the mixture of carbonyl compounds prepared according to embodiment 1 and having the following composition: 50 mol. % methyl ethyl ketone, 12.8 mol. % acetone, 3.4 mol. % n-butanal, 3.6 mol. % i-butanal, 14.5 mol. % propanal, and 15.7 mol % acetaldehyde, are kept in a flask with a reflux condenser at a temperature of 5° C. with stirring in the presence of 1 g NaOH and 1 ml H$_2$O for 10 hours. The temperature is then raised stepwise to 22° C. and up to 40° C. and is maintained, in order to carry out aldol condensation reactions, for 1 hour and 3 hours, respectively, at each temperature. After the aqueous phase is separated, the organic fraction is dried by maintaining in the presence of dry calcium chloride at room temperature for 10 hours, followed by filtration and isolation of a mixture of condensed carbonyl compounds. The group composition of the obtained product was determined according to the data of the chromatography-mass spectrometry analysis and is given in Table 3. The octane number of 10 wt % obtained HOC with gasoline AI-92 (92.5 RON and 83.9 MON) is 93.7 RON and 84.7 MON with the oxygen content being 1.1 wt %. The content of actual tar is 193 mg/100 cm³. Thus, the blending octane number of the produced HOC is 104.5 RON and 84.8 MON.

Example 12

100 ml of the mixture of carbonyl compounds prepared according to embodiment 1 (Example 2) and having the following composition: 50 mol. % methyl ethyl ketone, 12.8 mol. % acetone, 3.4 mol. % n-butanal, 3.6 mol. % i-butanal, 14.5 mol. % propanal, and 15.7 mol. % acetaldehyde, are kept in a flask with a reflux condenser at a temperature of 20° C. with stirring in the presence of 3 g $NaHCO_3$ and 5 ml $H_2O$ for 10 hours. The temperature is then raised to 60° and maintained, in order to carry out aldol condensation reactions, for 3 hours. After the aqueous phase is separated, the organic fraction is dried by maintaining in the presence of dry calcium chloride at room temperature for 10 hours, followed by filtration and isolation of a mixture of condensed carbonyl compounds. The group composition of the obtained product was determined according to the data of the chromatography-mass spectrometry analysis and is given in Table 3. The octane number of 10 wt % obtained HOC with gasoline AI-92 (92.6 RON and 84.0 MON) is 93.8 RON and 84.8 MON with the oxygen content being 1.5 wt %. The content of existent gums is 0.4 mg/100 cm³. Thus, the blending octane number of the produced HOC is 104.6 RON and 92.0 MON.

Example 13

100 ml of the mixture of carbonyl compounds prepared according to embodiment 1 (Example 4) and having the following composition: 45.6 mol. % methyl ethyl ketone, 11.7 mol. % acetone, 3.1 mol. % n-butanal, 4.3 mol. % i-butanal, 14.0 mol. % propanal, 15.1 mol. % acetaldehyde, 3.2 mol. % dimethylcyclopropane, 3.0 mol. % other products, are kept in a flask with a reflux condenser at a temperature of 5° C. with stirring in the presence of 0.5 g ion-exchange resin Amberlyst 36 and 1 ml $H_2O$ for 5 hours. The temperature is then raised stepwise to 22° C., 50° C. and 7° C. and is maintained, in order to carry out aldol condensation reactions, for 1 hour at each temperature. After the aqueous phase is separated by freezing, the organic fraction is dried over calcium chloride at room temperature for 10 hours, followed by filtration and isolation of a mixture of condensed carbonyl compounds. The group composition of the obtained product was determined according to the data of the chromatography-mass spectrometry and is given in Table 3. The octane number of 6.6 wt % obtained HOC with gasoline AI-92 (92.6 RON and 84.0 MON) is 93.7 RON and 84.6 MON with the oxygen content being 1.3 wt %. The content of actual tar is 1.3 mg/100 cm³. Thus, the blending octane number of the produced HOC is 103.6 RON and 90.0 MON.

TABLE 1

Embodiment 1. Gas-phase oxidation of a butane-butylene mixture (BBM) with the butene content of 87.4% vol. % and the butane content of 12.1% (Examples 1 to 6) and a propane-propylene mixture (PPM) with the propylene content of 85 vol. % (Examples 7 to 8) with nitrous oxide. Feedstock mixture: 10 mol. % $N_2O$, 90 mol. % BBM/PPM; the volume flow rate of the mixture is 25 cm³/min (under normal conditions).

| | | | | | | Characteristics of the process for producing a high-octane component | | | | | | | | | Characteristics of a high-octane component | | |
|---|---|---|---|---|---|---|---|---|---|---|---|---|---|---|---|---|---|
| | | | | | | | | Selectivity, S, % | | | | | | | Blending octane number | Oxygen content, | Content of actual tar, |
| No. | P, atm | T, °C. | $X_{N2O}$, % | $X_R$, % | Pr, g/l-h | $C_5$ | AA | PA | i-BA | A | BA | MEK | Other products | $S_Σ^{b)}$, % | RON | MON | wt % | mg/ 100 ml |
| 1 | 1 | 400 | 0.7 | 0.1 | 0.1 | 0.0 | 11.3 | 17.5 | 4.6 | 17.5 | 4.3 | 44.8 | 0.0 | 100 | 122.1 | 113.7 | 1.2 | 1.8 |
| 2 | | 500 | 10.6 | 1.4 | 1.8 | 0.0 | 7.9 | 16.0 | 5.8 | 13.3 | 2.3 | 48.5 | 6.2 | 93.8 | 120.1 | 109.5 | 2.2 | 2.0 |
| 3 | | 550 | 33.5 | 4.2 | 4.4 | 0.0 | 6.0 | 13.2 | 4.6 | 12.4 | 1.3 | 39.5 | 23.0 | 77.1 | 118.1 | 101.7 | 2.1 | 2.7 |
| 4 | 10 | 400 | 42.5 | 5.9 | 7.4 | 3.2 | 15.1 | 14.0 | 4.3 | 11.7 | 3.1 | 45.6 | 3.0 | 93.8 | 124.1 | 109.7 | 2.4 | 0.8 |
| 5 | 70 | 400 | 98.3 | 13.7 | 770.1 | 5.5 | 16.3 | 7.1 | 2.4 | 7.8 | 2.4 | 39.9 | 18.5 | 76.0 | 124.1 | 117.7 | 2.2 | 0.9 |
| 6[a)] | 10 | 400 | 31.0 | 17.1 | 16.4 | 5.6 | 15.2 | 14.1 | 3.9 | 12.1 | 2.9 | 43.9 | 2.3 | 92.1 | 122.1 | 109.7 | 2.3 | 1.2 |
| 7[c)] | 4 | 350 | 2.4 | 0.4 | 0.3 | 3.3 | 37.2 | 16.8 | — | 32.7 | — | — | 10.0 | 86.7 | 136.1 | 119.7 | 2.7 | 0.8 |
| 8[c)] | 7 | 450 | 74.5 | 12.5 | 10.3 | 6.1 | 21.3 | 16.5 | — | 36.8 | — | — | 19.2 | 74.6 | 130.1 | 113.7 | 2.2 | 1.0 |

[a)]feedstock mixture composition is 30% $N_2O$ + 70% BBM;
$C_5$—cyclopropane derivatives;
AA—acetalaldehyde;
PA—propanal;
i-BA—isobutanal;
A—acetone;
BA—butanal;
MEK—methyl ethyl ketone;
[b)]total selectivity to carbonyl products ($S_Σ$);
[c)]gas-phase oxidation of the propane-propylene mixture (PPM).

TABLE 2

Hydrogen influence on the catalytic properties of copper-containing catalysts in the methylation reaction of a mixture of ketones and aldehydes obtained according to embodiment 1 (temperature of 250° C., feedstock reaction mixture composition: 60% methanol, 20% HOC1, hydrogen as given in the table, the balance being Ar)

Characteristics of the process for producing a high-octane component

| No. | Molar composition of a catalyst | Contact time, s | Hydrogen concentration in the feedstock mixture, vol. % | Starting selectivity of the conversion of the HOC1 mixture to methylated $C_4$-$C_9$ products, % | Starting productivity, kg $C_4$-$C_9$ ketones by kg catalyst per hour | Time to a twofold reduction of the productivity, h | Blending octane number RON | MON | Oxygen content, wt % | Content of actual tar, mg/100 ml |
|---|---|---|---|---|---|---|---|---|---|---|
| 9 | 0.5•CuO•$Al_2O_3$ | 1.7 | 0 | 87 | 0.98 | 20 | 118.3 | 96.9 | 1.4 | 3.1 |
| 10 | 0.5•CuO•$Al_2O_3$ | 1.7 | 4 | 81 | 1.1 | 80 | 104.7 | 87.0 | 1.6 | 1.2 |

EMBODIMENT 3

Example 14

70 ml/min of the mixture of carbonyl compounds obtained at the second stage of the synthesis of the HOC according to embodiment 2 (10 vol. %) and hydrogen (80 vol. %) in argon (10 vol. %) is passed through a catalyst bed (1 gram) at a temperature of 160° C. for 10 hours. A catalyst of 15 wt % Ni on γ-$Al_2O_3$ is used as the catalyst. The reaction mixture composition is determined by a direct sampling from the vapor-gas flow with a subsequent analysis of organic components in a flame ionization detector and inorganic components in two thermal conductivity detectors. The organic components of the reaction mixture are separated in a capillary column DB 1701. The final mixture contains unreacted hydrogen and carbonyl compounds, tertiary, secondary and primary aliphatic alcohols, saturated hydrocarbons of a normal and iso-structure.

Conversion ($X_K$) of the carbonyl compounds (in percents), taking into account the change in the volume of the reaction mixture, is calculated by the formula:

$$Xk = 100 \cdot \frac{C_K^\circ - \beta \cdot C_K}{C_K^\circ}, \quad (2.2)$$

wherein: $C^\circ_K$ and $C_K$ are molar fractions of the carbonyl compounds in the starting and final reaction mixtures, respectively; β is the coefficient of volume change during the course of the reaction, which is calculated by the formula:

$$\beta = C^\circ_{Ar}/C_{Ar} \quad (2.3)$$

where: $C^\circ_{Ar}$ is a molar fraction of argon in the starting reaction mixture, %; $C_{Ar}$ is a molar fraction of argon in the final reaction mixture, relative units.

Catalyst productivity (Pr) for alkanes or alcohols in kg(product)/kg(cat.)·h is calculated by the formula:

$$Pr = \frac{1}{\beta} \cdot \frac{C_{product}}{100} \cdot \frac{F}{m} \cdot \frac{100.2 * 3600}{22414}, \quad (2.4)$$

wherein: β is the coefficient of volume change during the course of the reaction, calculated by the formula (2.3);

$C_{product}$ is a molar fraction of the product (hydrocarbons or alcohol) in the final reaction mixture, %;
F is the volumetric flow rate of the reaction mixture, $cm^3$/s;
m is a catalyst weight, g.

Selectivity (S) of the formation of alkanes or alcohols from the mixture of carbonyl compounds (in percents) is calculated by the formula:

$$S = 100 \cdot \frac{\beta \cdot C_{product}}{C_{ketone} - \beta \cdot C_{ketone}}, \quad (2.5)$$

wherein: β is the coefficient of volume change as a result of the reaction, calculated by the formula (2.3), relative units; $C_{product}$ and $C_{ketone}$ are molar fractions of the products and the starting carbonyl compounds, respectively, in the reaction mixture at the reactor outlet, %.

The results are given in Table 4.

The composite composition, conversion conditions, conversion of carbonyl compounds, selectivity of conversion of carbonyl compounds to the corresponding alcohols and alkanes, as well as to the by-products of isomerization, demethylation, cracking, and condensation are given here. One can see that the conversion of carbonyl compounds in the presence of a nickel catalyst is 58%. The main product of the conversion with a nickel catalyst is alcohol that is formed with a selectivity of 94 mol. %, followed by by-products that are mainly represented by cracking and condensation products. Alkanes are formed with a selectivity of only 1 mol. %. The octane number of the mixture of 10 wt % HOC with gasoline AI-92 (92.6 RON and 84.0 MON) is 93.5 RON and 85.5 MON with the oxygen content being 1.8 wt %. The content of actual tar is 3.5 mg/100 $cm^3$. Thus, the blending octane number of the obtained HOC is 110.6 RON and 94.0 MON.

Example 15

The reaction is carried out in the same manner as in Example 14, with the difference being that a composite that is a mechanical mixture of a nickel catalyst (1 g) and a zeolite with a structure (1 g) is charged to the reactor instead of a nickel catalyst. One can see that the replacement of the nickel catalyst by the composite results in an increase in the conversion of the starting carbonyl compounds, wherein a mixture of hydrocarbons of a normal and iso-structure is formed as the main products. The octane number of the mixture of 10 wt % HOC with gasoline AI-92 (92.0 RON and 83.9 MON) is 92.1 RON and 83.7 MON with the oxygen content being 0.1 wt %. The content of actual tar is 1.5 mg/100 cm³. Thus, the blending octane number of the produced HOC is 95.0 RON and 83.7 MON.

Example 16

The reaction is carried out in the same manner as in Example 15, with the difference being that the process is carried out at a temperature of 200° C. One can see that an increase in the temperature results in a small increase in the conversion, and, at the same time, a significant increase in the formation of alcohols is observed. Thus, the selectivity of the conversion of the mixture of carbonyl compounds to alcohols increases to 24%, and the selectivity of the conversion to hydrocarbons decreases from 94% to 70%. The octane number of the mixture of 10 wt % HOC with gasoline AI-92 (92.0 RON and 83.9 MON) is 92.6 RON and 84.5 MON with the oxygen content being 0.34 wt %. The content of actual tar is 2.1 mg/100 cm³. Thus, the blending octane number of the obtained HOC is 98.0 RON and 84.6 MON.

Example 17

The reaction is carried out in the same manner as in Example 15, with the difference being that Cu/Al₂O₃ is used as a catalyst. One can see that a copper catalyst is less active, as compared with a nickel catalyst, with respect to the hydrogenation to hydrocarbons. The product is a mixture of alcohols, hydrocarbons and the starting carbonyl compounds. The octane number of the mixture of 10 wt % HOC with gasoline AI-92 (92.0 RON and 83.9 MON) is 93.2 RON and 85.0 MON with the oxygen content being 0.7 wt %. The content of actual tar is 2.4 mg/100 cm³. Thus, the blending octane number of the produced HOC is 104.0 RON and 85.2 MON.

Example 18

The process is carried out similarly to Example 14, with the difference being that the HOC product obtained according to embodiment 1 is taken as a feedstock mixture of carbonyl compounds, i.e. the product of oxidation of a butane-butylene fraction (BBF) of the catalytic cracking with the following composition: 50 mol. % methyl ethyl ketone, 12.8 mol. % acetone, 3.4 mol. % n-butanal, 3.6 mol. % i-butanal, 14.5 mol. % propanal, and 15.7 mol. % acetaldehyde, and a mixture of 10 vol. % carbonyl compounds with 90 vol. % hydrogen is fed to the reactor. A pressure in the reactor is 10 atm. As a result of hydrogenation, conversion of carbonyl compounds was 100%, and selectivity to alcohols was 95%, hydrocarbons were not formed. The results are given in Table 4. The octane number of the mixture of 10 wt % HOC with gasoline AI-92 (92.6 RON and 84.0 MON) is 94.5 RON and 85.1 MON with the oxygen content being 2.3 wt %. The content of actual tar is 1.0 mg/100 cm³. Thus, the blending octane number of the obtained HOC is 111.6 RON and 95.0 MON.

Example 19

The process is carried out in the same manner as in Example 18, with the difference being that the temperature in the reactor is maintained at 150° C. As a result of hydrogenation, the total conversion of carbonyl compounds was 90%, and selectivity to alcohols was 95%, hydrocarbons were not formed. The conversion of aldehydes and lower ketones was 100%, and the conversion of methyl ethyl ketone was 80%. The results are given in Table 4. The octane number of the mixture of 10 wt % HOC with a gasoline fraction of the catalytic cracking (92.3 RON and 84.1 MON) is 94.6 RON and 85.2 MON with the oxygen content of 2.4 wt %. The content of actual tar is 1.2 mg/100 cm³. Thus, the blending octane number of the produced HOC is 112.3 RON and 95.1 MON.

TABLE 3

Embodiment 2. Production of a HOC by aldol condensation of the mixture of carbonyl compounds prepared according to embodiment 1 with various catalysts.

Characteristics of the process for producing a high-octane component

| | | | Composition of products of aldol condensation of producing a HOC according to embodiment 2, mol. % | | | | | | | | | | Characteristics of the high-octane component | | |
| --- | --- | --- | --- | --- | --- | --- | --- | --- | --- | --- | --- | --- | --- | --- | --- |
| | | | Unsaturated carbonyl compounds | | Hydroxy carbonyl compounds | | Paraldehyde and derivatives thereof | Unreacted components of the HOC1[a)] | | | | | Blending octane number | Oxygen content, | Content of existent gums mg/ |
| No. | T, ° C. | Catalyst | Aldehydes | Ketones | Aldehydes | Ketones | | AA | PA | BA | i-BA | A | MEK | RON MON | wt % | 100 ml |
| 11 | 40 | NaOH | 31 | 31 | 0 | 0 | 0.7 | 0.2 | 0.3 | 1.3 | 1.0 | 3.8 | 9.3 | 104.5 84.8 | 1.1 | 193 |
| 12 | 60 | NaHCO₃ | 2.5 | 0 | 19 | 0 | 2.5 | 1.8 | 4.0 | 6 | 6 | 11 | 21 | 104.6 92 | 1.5 | 0.4 |
| 12 | 70 | Amberlyst | 10.4 | 1.6 | 6.5 | 0 | 0 | 0.3 | 4.9 | 10.0 | 7.8 | 0.3 | 35.8 | 103.6 90.0 | 1.3 | 1.3 |

[a)]AA is acetaldehyde; PA is propanal; BA is butanal; i-BA is isobutanal; A is acetone, MEK is methyl ethyl ketone

TABLE 4

Embodiment 3. Results of hydrogenation of the high-octane component according to embodiments 1 and 2 over the composite "hydrogenation catalyst + dehydration catalyst" (weight ratio (hydrogenation catalyst)/(dehydration catalyst) = 1)

Characteristics of the process for producing a high-octane component

| | | | | | S, mol. % | | | Pr, kg product by kg hydr. cat. per hour | | Characteristics of a high-octane component | | | |
|---|---|---|---|---|---|---|---|---|---|---|---|---|---|
| | | | | | | | | | | Blending octane number | | Oxygen content, | Content of existent gums, |
| No. | Catalyst | T, °C. | P, atm | $X_k$, mol. % | Alcohol | Alkane | By-products | Alcohol | Alkane | RON | MON | wt % | mg/100 ml |
| 14 | Ni/Al$_2$O$_3$ | 160 | 1 | 58 | 94 | 1 | 5 | 1.02 | 0.01 | 110.6 | 94.0 | 1.8 | 3.5 |
| 15 | Ni/Al$_2$O$_3$ | 160 | 1 | 99.5 | 0 | 94 | 6 | 0 | 1.54 | 95.0 | 83.7 | 0.1 | 1.5 |
| 16 | Composite Ni/Al$_2$O$_3$-MFI | 200 | 1 | 99.99 | 23.9 | 70 | 6.1 | 0.37 | 1.08 | 98.0 | 84.6 | 0.34 | 2.1 |
| 17 | Composite CU/Al$_2$O$_3$-MFI | 160 | 1 | 60 | 25 | 67 | 8 | 0.39 | 1.03 | 104.0 | 85.2 | 0.7 | 2.4 |
| 18 | Ni/Al$_2$O$_3$ | 160 | 10 | 100 | 95 | 0 | 5 | 1.2 | 0 | 111.6 | 95.0 | 2.3 | 1.0 |
| 19 | Ni/Al$_2$O$_3$ | 150 | 10 | 90 | 95 | 0 | 5 | 1.08 | 0 | 112.3 | 95.1 | 2.4 | 1.2 |

The invention claimed is:

1. A method for producing a high-octane component of motor fuels from olefin-containing gas mixtures characterized in that an olefin-containing mixture comprising C2-C4 alkanes and olefins is oxidized with nitrous oxide, followed by an isolation of a product mixture as the high-octane component.

2. The method of claim 1, characterized in that a catalytic cracking gas is used as the olefin-containing mixture.

3. The method of claim 1, characterized in that the method is carried out at a temperature of 300 to 550° C. and a pressure of 1 to 100 atm is maintained.

4. The method of claim 1, characterized in that a volume ratio of the olefin containing mixture to the nitrous oxide is maintained at a level of 2 to 10.

5. A method for producing a high-octane component of motor fuels from olefin containing gas mixtures, characterized in that an olefin-containing gas mixture comprising C2-C4 alkanes and olefins is oxidized with nitrous oxide in a gas phase at the first stage, and then, at the second stage, the products obtained at the first stage are condensed, followed by an isolation of a product mixture as the high-octane component.

6. The method of claim 5, characterized in that a catalytic cracking gas is used as the olefin-containing mixture.

7. The method of claim 5, characterized in that the first stage is carried out at a temperature of 300 to 550° C., and the second stage is carried out at a temperature of 30 to 400° C., a pressure of 1 to 100 atm is maintained at the first stage, and a pressure of 1 to 10 atm is maintained at the second stage.

8. The method of claim 5, characterized in that a volume ratio of the olefin containing mixture to the nitrous oxide is maintained at a level of 2 to 10 at the first stage.

9. The method of claim 5, characterized in that the products of the oxidation of the olefin fraction, before being used as a feedstock at the second stage, are separated into aldehyde and ketone fractions.

10. The method of claim 9, characterized in that the ketone and aldehyde fractions are subjected to the condensation process separately.

11. The method of claim 9, characterized in that the ketone fraction is directly used as a high-octane component, and the aldehyde fraction is subjected to the condensation process.

12. The method of claim 5, characterized in that the products of the oxidation of the olefin fraction, before being used as a feedstock at the second stage, are separated into separate components, followed by using them as a target product and/or using as a feedstock for the condensation process.

13. The method of claim 5, characterized in that the second stage is carried out in a liquid phase by aldol or aldol-crotonic condensation in the presence of any known catalyst.

14. The method of claim 5, characterized in that the second stage is carried out by condensation with methanol in a gas phase in the presence of a copper-containing catalyst at a volume ratio of the product mixture obtained at the first stage to methanol of 1 to 10.

15. The method of claim 14, characterized in that, at the second stage, the condensation of the products obtained at the first stage with methanol is carried out in the presence of at least 0.1 vol. % hydrogen.

16. The method of claim 14, characterized in that, at the second stage, the condensation of the products obtained at the first stage with methanol is carried out in the presence of a catalyst containing 5 to 40 wt % copper on a support.

17. The method of claim 16, characterized in that the catalyst support used at the second stage is Al$_2$O$_3$ and/or SiO$_2$ and/or TiO$_2$ and/or aluminosilicate and/or silicate or aluminosilicate glass fibers.

18. A method for producing a high-octane component of motor fuels from olefin-containing gas mixtures, characterized in that an olefin-containing mixture comprising C2-C4 alkanes and olefins is oxidized with nitrous oxide in a gas phase at the first stage, and then, at the second stage, the products obtained at the first stage are condensed, and, at the third stage, the mixture of condensed oxygenates obtained at the second stage or the mixture of carbonyl compounds obtained at the first stage are reacted with hydrogen in the presence of a hydrogenation catalyst, followed by an isolation of a mixture of hydrogenated products as the high-octane component.

19. The method of claim 18, characterized in that a catalytic cracking gas is used as the olefin-containing mixture.

20. The method of claim 18, characterized in that the first stage is carried out at a temperature of 300 to 550° C., the second stage is carried out at a temperature of 30 to 400° C., and the third stage is carried out at a temperature of 100 to 400° C.

21. The method of claim 18, characterized in that a pressure of 1 to 100 atm is maintained at the first stage, a pressure of 1 to 10 atm is maintained at the second stage, and a pressure of 1 to 100 atm is maintained at the third stage.

22. The method of claim 18, characterized in that a volume ratio of the olefin-containing gas mixture to the nitrous oxide is 2 to 10 at the first stage.

23. The method of claim 18, characterized in that the products of the oxidation of the olefin fraction, before being used as a feedstock at the second stage, are separated into aldehyde and ketone fractions.

24. The method of claim 18, characterized in that the ketone and aldehyde fractions are subjected to the condensation process separately.

25. The method of claim 18, characterized in that the ketone fraction is directly used as a high-octane component, and the aldehyde fraction is subjected to the condensation process.

26. The method of claim 18, characterized in that the products of the oxidation of the olefin fraction, before being used as a feedstock at the second stage, are separated into separate components, followed by using them as a target product and/or using as a feedstock for the condensation process.

27. The method of claim 18, characterized in that the second stage is carried out in a liquid phase by aldol or aldol-crotonic condensation in the presence of any known catalyst.

28. The method of claim 18, characterized in that the second stage is carried out by condensation with methanol in a gas phase in the presence of a copper-containing catalyst at a volume ratio of the product mixture obtained at the first stage to methanol of 1 to 10.

29. The method of claim 18, characterized in that a volume ratio of the mixture of the condensed products obtained at the second stage to hydrogen of 1 to 10 is maintained at the third stage.

30. The method of claim 18, characterized in that the second stage is carried out in the presence of a catalyst containing 5 to 40 wt % copper on a support, and the third stage is carried out in the presence of a hydrogenation catalyst containing 5 to 40 wt % nickel, and/or 5 to 40 wt % copper, and/or 5 to 40 wt % cobalt, and/or 0.3 to 2 wt % palladium, and/or 0.3 to 2 wt % platinum, and/or 0.3 to 2 wt % gold on a support.

31. The method of claim 30, characterized in that $Al_2O_3$ and/or $SiO_2$ and/or $TiO_2$ and/or aluminosilicate and/or silicate or aluminosilicate glass fibers are used as a catalyst support at the second and third stages.

32. The method of claim 30, characterized in that the third stage is carried out in the presence of a mechanical mixture of a hydrogenation catalyst and an acid catalyst, with H-form zeolite selected from zeolites having FAU, FER, MFI, MEL, BEA, MTT, and TON structures being used as the latter.

* * * * *